United States Patent
Strychacz et al.

(10) Patent No.: US 7,933,645 B2
(45) Date of Patent: Apr. 26, 2011

(54) USE OF EEG TO MEASURE CEREBRAL CHANGES DURING COMPUTER-BASED MOTION SICKNESS-INDUCING TASKS

(75) Inventors: Chris Strychacz, San Diego, CA (US); Erik Viirre, San Diego, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 846 days.

(21) Appl. No.: 11/398,737

(22) Filed: Mar. 30, 2006

(65) Prior Publication Data
US 2006/0241373 A1 Oct. 26, 2006

Related U.S. Application Data

(60) Provisional application No. 60/666,591, filed on Mar. 31, 2005.

(51) Int. Cl.
*A61B 5/04* (2006.01)

(52) U.S. Cl. ....... 600/544; 600/545
(58) Field of Classification Search ......... 600/544, 600/545, 558
See application file for complete search history.

(56) References Cited

U.S. PATENT DOCUMENTS

| | | | | |
|---|---|---|---|---|
| 4,413,522 | A * | 11/1983 | Leatherwood et al. | 73/646 |
| 4,967,038 | A * | 10/1990 | Gevins et al. | 600/383 |
| 5,694,939 | A * | 12/1997 | Cowings | 600/484 |
| 2003/0144829 | A1* | 7/2003 | Geatz et al. | 703/22 |
| 2004/0249422 | A1* | 12/2004 | Gliner et al. | 607/58 |
| 2005/0240253 | A1* | 10/2005 | Tyler et al. | 607/134 |
| 2006/0235331 | A1* | 10/2006 | Kiderman | 600/558 |

FOREIGN PATENT DOCUMENTS

SU 1724173 A1 * 4/1992

OTHER PUBLICATIONS

Bird et al, Biofeedback training of 40-Hz EEG in Humans, 1978, Plenum Publishing Corporation, Biofeedback and Self-Regulation, vol. 3, No. 1, pp. 1-11.*

Odkvist, Projection of the Vestibular Nerve to the Area 3a Arm Field in the Squirrel Monkey (*Saimiri sciureus*), Mar. 12, 1974, Exp. Brain Res. 21. p. 97-105.*

* cited by examiner

*Primary Examiner* — Tse Chen
*Assistant Examiner* — Jacqueline Cheng
(74) *Attorney, Agent, or Firm* — Joseph K. Hemby, Jr.; Albert M. Churilla; Ning Yang

(57) ABSTRACT

The invention relates to a method of determining early onset of motion sickness by brain imaging. The method discloses an objective means of determining the onset of motion sickness by evaluating a specific region of the brain. The method can also be utilized in evaluating the predisposition toward motion sickness in workers in occupations prone to motion sickness.

4 Claims, 4 Drawing Sheets

USE OF EEG TO MEASURE CEREBRAL CHANGES DURING COMPUTER-BASED MOTION SICKNESS-INDUCING TASKS

CROSS-REFERENCES TO RELATED APPLICATIONS

This application claims priority to U.S. Provisional application 60/666,591 filed Mar. 31, 2005.

BACKGROUND OF INVENTION

1. Field of Invention

The inventive subject matter relates to a method of utilizing EEG imaging for detection of marker of motion sickness. The inventive subject matter also relates to a method for the discrimination of individuals likely to be susceptible to motion sickness and to a method to evaluate the efficacy of therapeutic interventions aimed at preventing or mitigating motion sickness.

2. Background Art

An objective method for the determination of motion sickness is of importance in evaluating predisposition of individuals to motion sickness in occupations such as aircraft pilots, shipboard personnel. Evaluating onset of motion is also vital in evaluating pharmaceuticals aimed at mitigating the physical effects of motion sickness and at assessing contraindications of new drugs. Additionally, the design of vehicles and motion simulators requires objective measures, verses self-reporting, of motion sickness.

Physiological markers of motion sickness include increase in skin conductance, gastric EEG (gastric tachyarrhythmia) and pallor. EEG markers for motion sickness, however, are unique among markers of motions sickness. Measuring markers of motion sickness by older EEG technologies suffered from poor resolution.

Human brain imaging techniques such as positron emission tomography (PET) and functional magnetic resonance imaging (fMRI) have dramatically increased our knowledge about neural activity related to cognitive and emotional processes (Ferrari, et al, 2004; Hoshi, 2003). fMRI, in particular, is reliable, safe and now gives very high resolution measures of neural activity. However, these brain imaging techniques have a number of disadvantages and limitations, including the fact that they are expensive, non-portable, confine participants to restricted positions, can involve considerable patient or equipment preparation times and involve moderate risk such as exposing people to potentially harmful materials (PET) or loud noises (fMRI)(Ferrari, et al, 2004; Jasdzewsk et al, 2003). An important disadvantage of PET and MRI imaging techniques, however, is that they are not suitable for many uses, including the continuous monitoring and identification of functional brain activation related to cognitive activity and ongoing operator states in natural environments.

New developments in miniaturization make current electro-encephalography (EEG) systems highly operable and reliable. In particular, the two advances of placing the amplifier directly on the electrode and new mathematical techniques for data analysis make EEG much more suitable than previous iterations. The miniature amplifiers provide large signal to noise rations and the analytic techniques bring out signals of interest.

Non-invasive optical methods, such as the use of functional near-infrared spectroscopy (fNIRS) have increasingly been used to investigate functional activation of the human cortex by mapping cortical oxygenation changes (Hoshi, 2003; Obrig and Villringer, 2003). When compared to brain imaging techniques such as MRI and PET, fNIRS is a low cost, low risk, negligibly invasive and portable technology. This makes fNIRS suitable for the study of cerebral changes under many real world conditions (e.g. filed studies, computer operation) and situations requiring continuous monitoring, repeated sessions, or the monitoring of infants and children. Another advantage of fNIRS is that it can be used in conjunction with other brain imaging technologies such as EEG (Obrig and Villringer, 2003) or PET (Villringer, et al, 1997). Combining EEG and fNIR technologies together may enable investigations of the coupling between neuronal and vascular responses to functional brain activation. The ease of application of fNIR compared to EEG makes fNIRS advantageous for use in monitoring operators.

While there is a relative paucity of research on EEG changes associated with motion sickness, several studies have been conducted. Chelen, et al used precoriolis stimulation through to imminent emesis and found that several EEG changes occurred in the temperofrontal region when compared with baseline. These changes included an increase in the mean power spectral energy in the delta band (0-2 Hz) during sickness by a factor of 13.7 and mean theta (3-7 HZ) increases by a factor of 2.2. Chelen and associates reported that these changes also correlated with the level of self-reported MS symptoms. They asserted that these changes (particularly delta band changes) indicate that low frequency oscillatory stimulation is being diffusely projected about the central nervous system.

Hu, et al compared a variety of physiological measures associated with MS, including gastric, myoelectric, electrodermal, cardiovascular and brain electrical activities. While they reported an increase in 4-9 cpm activity (gastric tachyarrhythmia) was the most sensitive physiological index of the severity of motion sickness symptoms, significant increases in EEG activity of the 0.5 to 4 Hz frequency band (delta) also occurred.

Dornhoffer, et al studied Sopite syndrome, a syndrome commonly associated with motion sickness that is characterized by a loss of initiative, sensitivity to normally innocuous sensory stimuli, and impaired concentration amounting to a sensory gating deficit. They used a rotary chair to elicit the sensory mismatch that occurs during motion sickness by over stimulating the vestibular apparatus and measured the effects of rotation on the manifestation of the P50 midlatency auditory-evoked response as a measure of arousal and distractibility. They found that rotation-induced motion sickness produced no change in the level of arousal but did produce a significant deficit in sensory gating. This indicates that some of the attentional and cognitive deficits observed with motion sickness may be due to distractibility induced by decreased habituation to repetitive stimuli.

De Metz, et al found that Fast Fourier analysis of the EEG activity showed more asymmetry between the two hemispheres in subjects who suffered MS as compared with those who did not experience motion sickness. In another study, Min, et al. evoked simulator sickness using a graphic simulator while monitoring EEG. They found that scores on a Simulator Sickness Questionnaire (SSQ) correlated positively with delta/total, and negatively with theta/alpha and beta/total. SSQ scores also had significantly high negative correlations with theta total at both Fz and Cz.

Taken together, the earlier studies do not represent a uniformity of findings for EEG changes associated with motion sickness and may include a wide variety of artifacts. The lack of consistent observations as a predictor of a propensity toward motion sickness was the motivation behind the search for a more reliable methodology, which is an aspect of the current invention

SUMMARY OF INVENTION

Currently available method for the prediction of the early onset of motion sickness, including methods incorporation brain imaging technologies, are not suitable. Therefore, an object of this invention is an improved method determining the onset of motion sickness by a more refined focusing on relevant regions of the brain using electroencephalograph technology.

DESCRIPTION OF PREFERRED EMBODIMENTS

Figure 1:
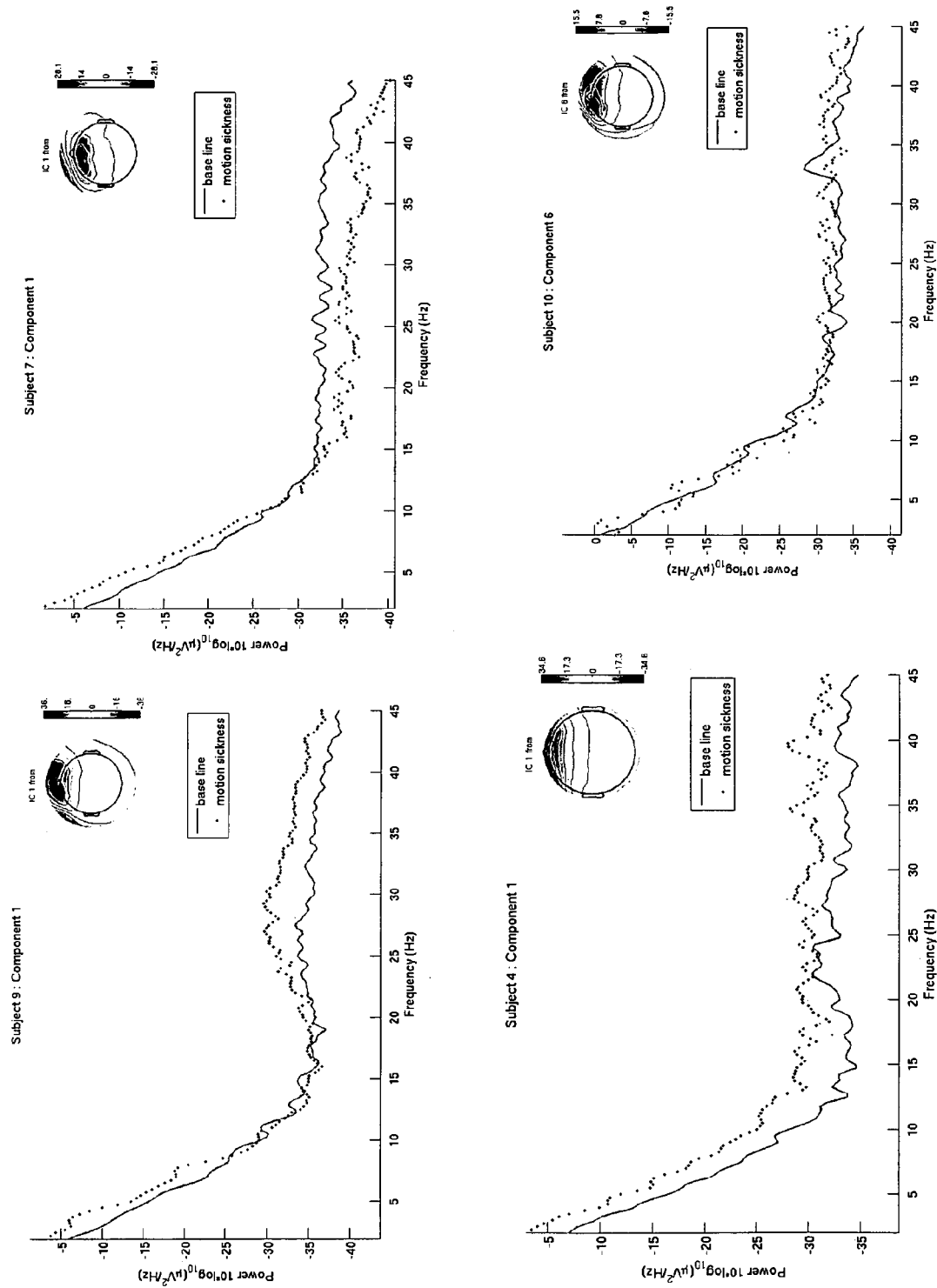
FIG. 1. Low frequency EEG activity attributable to eye movement.

Evaluation of individuals, in certain occupations, for a propensity to suffer from motion sickness requires an object determination of the early onset of motion sickness. Similarly, the study of new anti-motion sickness interventions requires reproducible and object analysis of motion sickness onset. However, previous imaging methods, used to determine the onset of motion sickness, have yielded inconsistent results and are, therefore, of limited value.

More refined methods of motion sickness are needed for these and other applications. An aspect of the current invention, therefore, is a method for evaluating of the onset of motion sickness incorporating a more refined determination of the relevant regions of the brain. The overall inventive method of objective determination of motion sickness comprises the identification of the suppression of 20 and 40 Hz peaks in the central posterior (occipital) region/ventral intraparietal area during the onset of motion sickness.

Applicants contemplate that the inventive method would be useful in a number areas including clinical evaluation and screening of patients suffering from motion sickness to occupational evaluation of astronauts, pilots and shipboard crews to the design of vehicles in order to minimize motion sickness and in the design of motion simulators.

In addition to identifying motion sickness onset, this method could lead to effective a biofeedback training techniques to prevent the onset of motion sickness in motion sick susceptible individuals or individuals who want to decrease their susceptibility to motion sickness. Individuals would first be taught to identify and discriminate 20 and 40 Hz peak states in non-motion and non-virtual moving environment using EEG biofeedback. An extensive (32-128 electrode) or selected array (4-16 electrodes) could be used to provide biofeedback for training. Individuals would next be exposed to a virtual motion (mildly nauseagenic) environment and practice maintaining or increasing 20 and 40 Hz peaks. Finally, the inventive method comprises having individuals practice maintaining or increasing 20 and 40 Hz peaks in actual motion environments.

EXAMPLE

The following example is provided to better illustrate the utility of the subject invention. In this example, subjects were recruited that had the following criteria:

a. Healthy male and female between ages 18 and 50 years old.

b. Motion sickness susceptible as determined by self-reported answers to the Motion History Questionnaire (MHQ). The MHQ was a version of the MHQ used by Kennedy and Graybiel, 1965.

c. Receipt of written clearance after an in-person neurological exam conducted by a medical monitor.

d. Right-handedness.

Subject exclusion criteria included pregnancy or any person currently on medication for motion sickness, taking sedatives, anticonvulsants, or stimulants, or with a history of seizure disorder, stroke, or brain injury.

The EEG of the subjects was recorded using the Biosemi ActiveTwo™ system (BioSemi, Amsterdam, Netherlands), equipped with 128-channels, a DC amplifier, 24-bit resolution, and a biopotential measurement system with active Ag/AgCl electrodes. The Active Two™ device features a stretchable head cap system that obtains reliable measurements without skin preparation. The amplifier for the electrodes are housed in the electrode casing, and the electrodes are positioned according to the 10-20-electrode system. Horizontal electrooculography (EOG) was recorded from one electrode placed at the outer canthi of the left eye. Vertical EOG was recorded from two electrodes placed on the infraorbital and supraorbital regions of the right eye in line with the pupil. EEG signals were band-pass filtered at a sampling rate of 256 Hz.

A flow filed video, used in the study, consisted of erratically rotating rectangles that were black and white with dots in them. The boxes appeared to diverge or converge as they rotated erratically. A ball-tracking task was used as a cognitive/behavioral performance measure. The task involved utilizing a computer mouse to move a ball projected onto a computer screen into the center of a fixed circle. The ball moved randomly in different directions on the screen and the user had to constantly move the computer mouse to relocate the ball within the center of the circle.

All potential subjects were first screened via telephone or in person and informed of their eligibility to participate immediately after completing the MHQ. The primary criteria for inclusion into the study was if subjects answered questions on the MHQ suggesting that they had a history of experiencing motion sickness while flying, riding as a passenger in an automobile or while on a boat/ship. Subjects who also indicated that they experienced motion sickness while viewing certain images on a computer, television or big screen movie were also considered susceptible to motion sickness. Subjects were asked to abstain from food and beverage for 2 hours prior to study participation in order to reduce the risk of vomiting.

Subjects were seated in a darkened room in a standard office swivel chair 5 feet from a wall that was used as a projection screen. A tape measure was used to measure the size of their head from nasium to inin in order to select the proper-sized EEG cap. The forehead region was scrubbed lightly with a sterile alcohol pad and a functional near-infrared spectroscopy (fNIRS) encasement containing an infrared emitter and detector was placed on the forehead with the detector placed 4 cm above the nasium and centered on the forehead. The emitter was placed 3 cm horizontal and to the right of the detector with the encasement for the fNIR emitter/ transducer initially held in place by double-sided tape. The EEG cap was then lapped over the fNIRS encasement and stretched over the ears and around and beyond the occipital protuberance. The EEG cap was used to pull the chinstrap on the EEG cap taut and affix the Velcro straps under their chin together. Approximately 120 of the 128 electrode holders of the EEG cap were then filled with EEG gel and the electrodes inserted. While checking the EEG electrodes, the ball-tracking task was explained to the subjects and they were allowed to practice the task for approximately 5 minutes.

As the brain monitoring equipment was being set up it was explained to the subjects that at several points during the experiment they would be asked to rate their sense of motion and degree of motion sickness on a scale of 0-3 by showing number of fingers.

After the brain monitoring equipment was recording the subjects were asked to close their eyes and raise their feet off the floor. To demonstrate motion sensation they were then rotated back and forth on their chair at approximately 0.5 Hz for 8-10 seconds. After rotating them they were asked to open their eyes and report the extent to which they felt as though they were still moving on the previously explained rating scale of 0-3. All subjects were videotaped and monitored in real-time to monitor subjects for signs of motion sickness.

The procedure for the study began with obtaining a 5-minute baseline that consisted of the subject sitting quietly while viewing a still screen capture of the flow field. This screen capture of the flow filed was immediately followed by 3 minutes of the ball-tracking task. Immediately after the ball-tracking task ended, Session 1 began with subjects viewing the moving flow filed (3 minutes). The flow field was then terminated, and 1 minute of the ball tracking-only task began. As the subject was performing the ball-tracking task the flow field also appeared on the screen after 1 minute and lasted for 3 minutes. Immediately after the combined task ended there was an assessment in which subjects were asked to rate their degree of motion sensation and motion sickness by showing a number of fingers or the "OK" sign for zero. The sequence for Session 1 was repeated for Session 2. Session 3 consisted of viewing the driving video for 90 seconds, stopping the video to assess motion sense and motion sickness and then performing the tracking task for 1 minute. This process was repeated for Session 4. For Session 5, subjects viewed the driving video for 3 minutes and then were assessed for motion sense and motion sickness.

Prior to EEG data analysis the following procedure was followed in preparing the data: 1) data were first visually inspected for bad channels and bad epochs, which were rejected; and 2) data were high passed for 1 Hz and low passed at 50 Hz.

Figure 2:
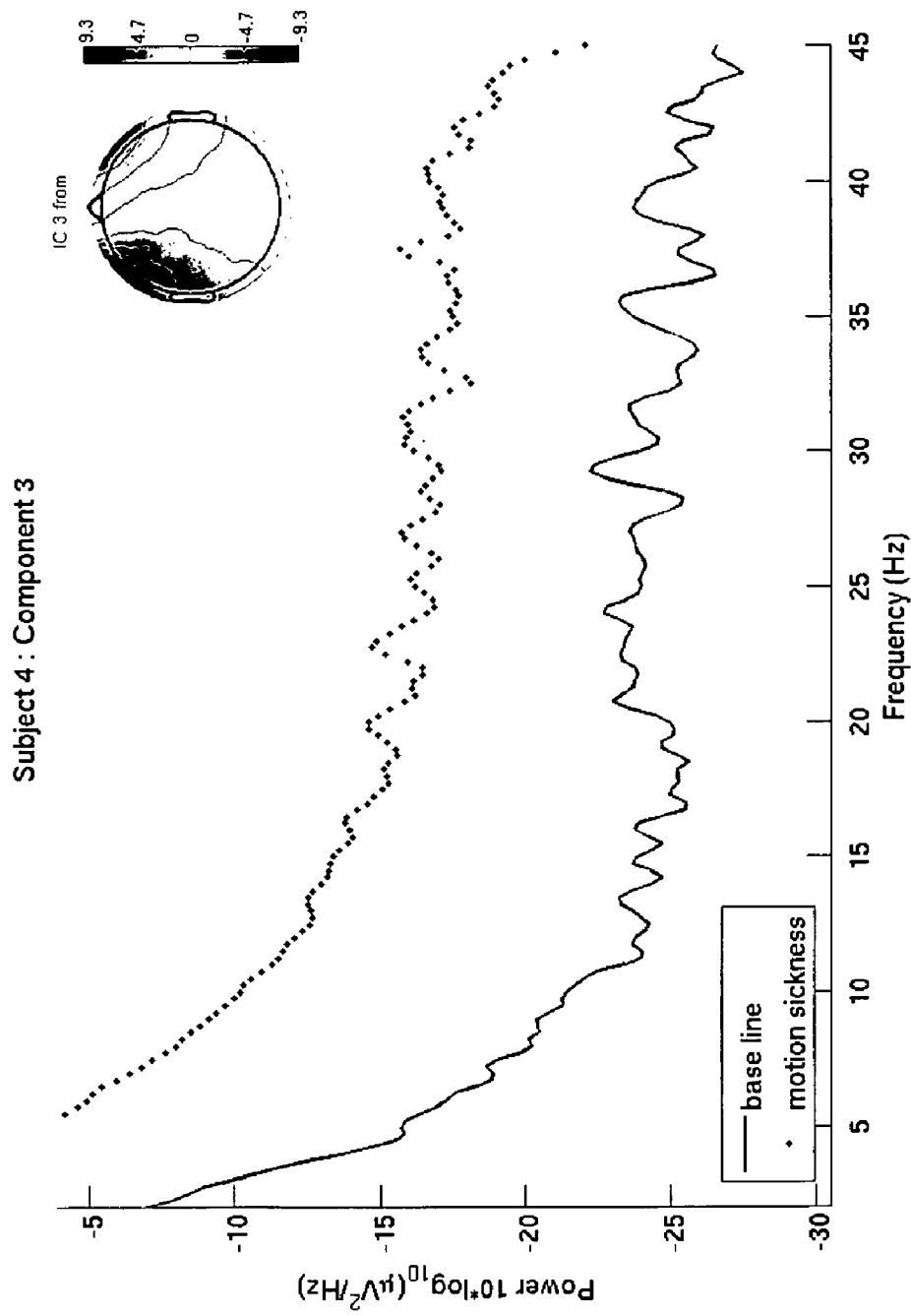
FIG. 2. Global increases in power spectra attributable to perspiration during motion sickness.

The largest amount of variance in EEG activity in 3 of 4 subjects corresponded to frontal activity (e.g. independent component #1), which was expected and typically is indicative of eye movement. As an illustration, the reader is referred to FIG. 1. These components show higher activity in motion sickness subjects in the range of 1-10 Hz. Subjects also tended to demonstrate increased spectral power across all frequencies in the range of 3 to 8 db when comparing baseline measures with motion sickness epochs, as illustrated in FIG. 2.

Figure 3:
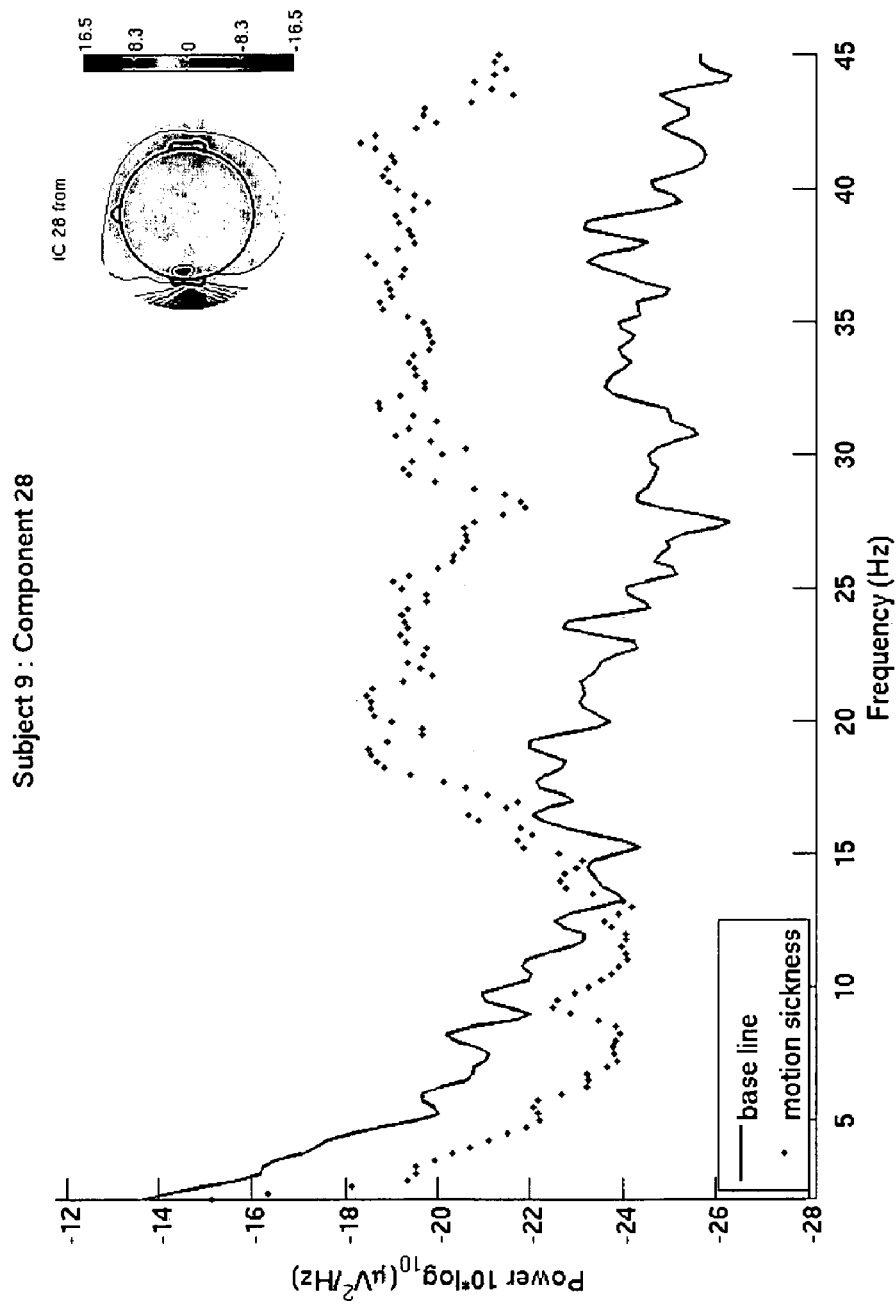
FIG. 3. Power spectral increases in the 20-50 Hz range during motion sickness attributable to skull muscular tension.

Some subjects demonstrated selective local increases in spectral power in the 20-50 Hz range, as illustrated in FIG. 3. The independent components demonstrating this effect appear to be external muscles on the skull. Some subjects reported jaw clenching and other muscle tension associated with their motion sickness.

Figure 4:
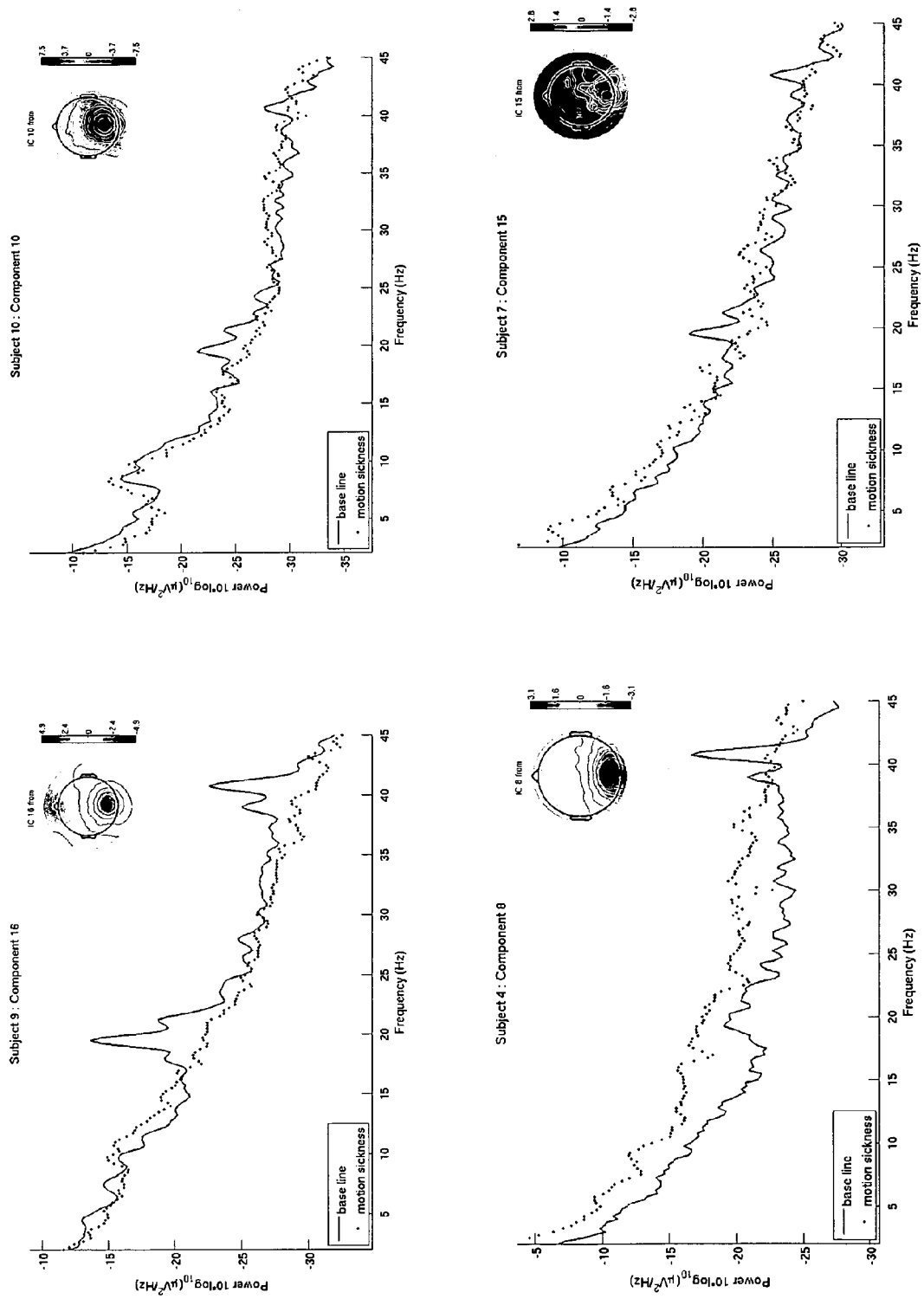
FIG. 4. Suppression of 20 and 40 Hz peaks in the central posterior region between baseline and motion sickness epochs.

There was a central posterior (occipital) independent component in our motion sickness subjects that shows 20 Hz and 40 Hz peaks in the baseline condition and the suppression of these peaks during the motion sickness condition. This observation is illustrated in FIG. 4.

REFERENCES

1. Chelen, W., M. Kabrisky, S. Rogers. 1993. Spectral analysis of the electroencephalographic response to motion sickness. Aviation Space Environmental Medicine. 64:24-29.
2. De Metz, K., O. Quadens, M. De Graaeve. 1994. Quantified EEG in different G situations. Acta Astronaut. 32:151-157.
3. Dornhoffer, J. N. Mamiya, P. Bray, R. Skinner, E. Garcia-Rill. 2003. Effects of rotation on the sleep state-dependent midlatency auditory evoked P50 potential in the human. Journal of Vestibular Research (2002-2003); 12:205-209.
4. Ferrari, M., L. Mottola, Q. Valentine. 2004. Principles, techniques and limitations of near infrared spectroscopy. Canadian Journal of Applied Physiology. 29:463-487.
5. Hoshi, Y. 2003. Functional near-infrared optical imaging: Utility and limitations in human brain mapping. Psychophysiology 40:511-520.
6. Jasdzewski, G., G. Strangman, J. Wagner, K. Kwong, R. Poldrack, D. Boas. 2003. Differences in the hemodynamic response to event-related motor and visual paradigms as measured by near-infrared spectroscopy. NeuroImage 20:479-488.
7. Min, B. S. Chung, Y. Min, K. Sakamoto. 2004. Psychophysiological evaluation of simulator sickness evoked by graphic simulator. Applied Ergonomics 35:549-556.
8. Obrig, H. A. Villringer. 2003. Beyond the visible-imaging the human brain with light. J. Cereb Blood Flow Metab. 23:1-18.
9. Villringer, A. 1997. Understanding functional neuroimaging methods based on neurovascular coupling. Adv. Exp. Med. Biol. 413:177-193.

Having described the invention, one of skill in the art will appreciate in the appended claims that many modifications and variations of the present invention are possible in light of the above teachings. It is therefore, to be understood that, within the scope of the claims, the invention may be practiced otherwise than as specifically described.

What is claimed is:

1. A method for determining onset of motion sickness of subjects comprising:
   measuring brain signals by electroencephalography in the central posterior/occipital region of the subjects;
   detecting presence of 20 and 40 Hz peaks to determine a baseline condition;
   analyzing the brain signals for suppression of said peaks;
   identifying the subjects whose brain signals show a suppression of said peaks as experiencing motion sickness.
2. The method of claim 1, wherein said subjects whose brain signals show a suppression of said peaks are determined unsuitable for motion sensitive occupations.
3. The method of claim 1, wherein said determination of onset of motion sickness is an input to virtual motion simulators, virtual motion computer programs, or vehicles.

4. A method for preventing or decreasing onset of motion sickness in a motion sick susceptible subject using electroencephalography biofeedback, comprising:
 a. measuring brain signals by electroencephalography in the central posterior/occipital region of the subject using a 32-128 electrode or selected array of 4-16 electrodes;
 b. detecting the presence of 20 and 40 Hz peaks from the electroencephalograph;
 c. providing instructions to said subject to identify and discriminate the 20 and 40 Hz peaks in a non-motion and non-virtual moving environment using electroencephalography biofeedback;
 d. exposing said subjects to a virtual motion environment, said subjects practicing maintaining or increasing said 20 and 40 Hz peaks in the virtual motion environment using electroencephalography biofeedback training; and
 e. exposing said subjects to an actual motion environment, said subjects practicing maintaining or increasing said 20 and 40 Hz peaks in the actual motion environment using electroencephalography biofeedback training.

* * * * *